United States Patent [19]

LaBate

[11] Patent Number: 4,481,809

[45] Date of Patent: Nov. 13, 1984

[54] METHOD AND APPARATUS FOR MONITORING EROSION IN GAS STIRRING DEVICES IN MOLTEN METAL LADLES

[76] Inventor: Micheal D. LaBate, 115 Hazen Ave., Ellwood City, Pa. 16117

[21] Appl. No.: 527,362

[22] Filed: Aug. 29, 1983

[51] Int. Cl.³ .............................................. G01N 17/00
[52] U.S. Cl. ............................................ 73/86; 266/99
[58] Field of Search .................. 73/86; 374/7; 266/99

[56] References Cited

U.S. PATENT DOCUMENTS

| | | | |
|---|---|---|---|
| 2,915,305 | 12/1959 | Craig | 73/86 |
| 3,024,657 | 3/1962 | Brown | 266/99 |
| 3,856,284 | 12/1974 | Hoyer | 266/99 |
| 3,898,366 | 8/1975 | Aurini | 266/99 |
| 4,249,719 | 2/1981 | Knuppel et al. | 266/99 |

FOREIGN PATENT DOCUMENTS 82078  6/1983  European Pat. Off. .

*Primary Examiner*—S. Clement Swisher
*Attorney, Agent, or Firm*—Harpman & Harpman

[57] ABSTRACT

A method and apparatus are disclosed for monitoring the condition of the stirring block and solid plug therein as incorporated in the normal refractory brick lining of a molten metal ladle to provide a structure through which gas can be introduced into the molten metal, the method utilizes heat sensors and/or Hall Effect transducers embedded in the stirring block and/or solid plug therein in connection with apparatus providing a warning of critical wear and/or erosion in the gas stirring devices by the molten metal in the ladle. An appropriately shaped stirring block provides for the positioning of some of the normal refractory brick lining of the ladle partially thereover so as to eliminate loosening or cracking of the stirring block and the undesirable escaping of molten metal from the ladle.

7 Claims, 4 Drawing Figures 4,481,809

METHOD AND APPARATUS FOR MONITORING EROSION IN GAS STIRRING DEVICES IN MOLTEN METAL LADLES

BACKGROUND OF THE INVENTION

1. Technical Field:

This invention relates to devices for insufflating gas into a mass of molten metal and apparatus associated therewith enabling the condition of the devices to be determined at a remotely located indicator.

2. Description of the Prior Art:

Prior structures of this type have generally employed permeable plugs through which the gas is introduced into the liquid. Such typical devices may be seen in U.S. Pat. Nos. 2,811,346, 2,947,527, 3,330,645, 3,610,602 and 3,343,829. None of the devices of the prior art provide any apparatus usable in a method of determining the condition of the stirring block or the plugs associated therewith through which the gas is introduced into the ladle.

The present invention introduces heat sensors into the body of the stirring block and into the body of the plug used therein to define the gas passageway into the ladle and connects the heat sensors to appropriate indicating apparatus whereby temperatures in the block and the plug rising above a predetermined normal level serve to indicate the condition of the block and plug. Alternately Hall Effect transducers may be advantageously employed for the same purpose.

SUMMARY OF THE INVENTION

A method and apparatus for monitoring erosion and likewear in gas stirring devices in molten metal ladles provides the stirring blocks and the plugs used in association therewith for defining gas passageways with heat sensors or Hall Effect transducers in appropriate circuits with apparatus registering changes in temperature or changes in the output of the transducers from a predetermined range indicating the degree of wear and/or erosion of the stirring block and plug associated therewith and the need of replacing the same to avoid the escape of molten metal as occurs when such wear and erosion reach the point where the gas being introduced is unable to prevent the flow of molten metal through or around the gas introducing devices.

DESCRIPTION OF THE PREFERRED EMBODIMENT

Figure 1:
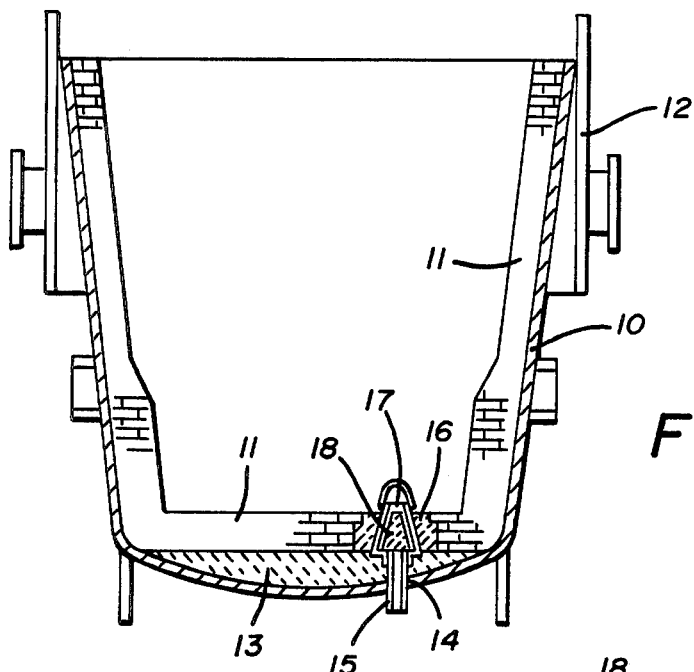
FIG. 1 is a cross sectional side elevation of a ladle showing the devices for introducing gas into molten metal installed in the refractory lining of the ladle.

In the form of the invention chosen for illustration herein, the method and apparatus for monitoring the condition of the stirring block and solid or gas defusing plug therein is generally illustrated in FIG. 1 of the drawings wherein a metal vessel 10 in the form of a ladle is provided with a refractory lining 11 such as formed of refractory brick or rammed refractory material, the ladle having support means 12 by which it is arranged to be pivoted so as to pour molten metal therefrom as known in the art.

The bottom portion of the metal vessel 10 has a first layer 13 of refractory material and the refractory brick lining 11 is positioned thereon. An opening 14 in the bottom of the ladle provides for the installation of a gas delivering tube 15 which extends upwardly through the refractory material 13 and communicates with a stirring block 16 which is surrounded by the refractory brick 11 forming the refractory lining of the ladle. The stirring block 16 has a central conical passageway 17 therethrough and a frusto-conical plug 18 positioned therein so as to form a passageway for gas introduced into the tube 15.

Figure 2:
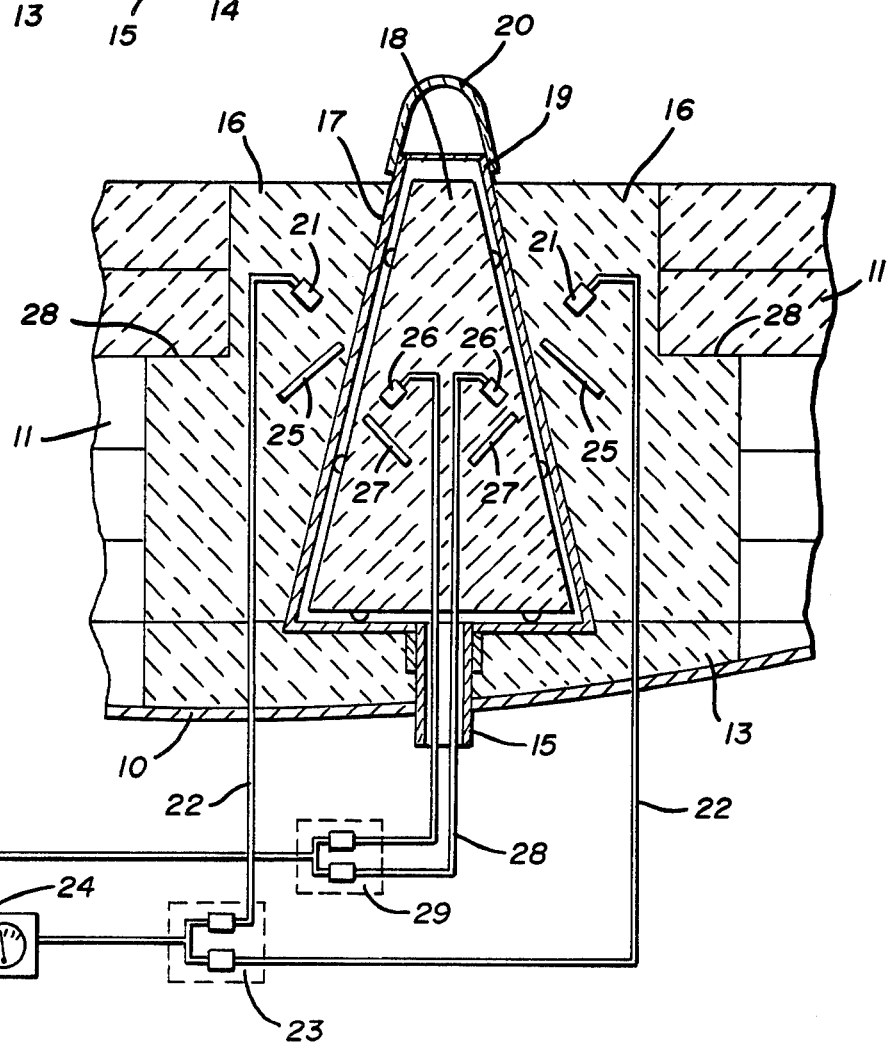
FIG. 2 is an enlarged cross sectional detail of an improved stirring block positioned in the refractory lining of a ladle and illustrating apparatus for determining wear or erosion occurring therein and in a plug positioned in the stirring block.

By referring to the drawings and FIG. 2 in particular it will be seen that the conical plug 18 is spaced with respect to a frustro-conical metal shell 19 which in turn is provided with a cap 20 as disclosed in my co-pending patent application Ser. No. 382,966 now U.S. Pat. No. 4,396,179.

Still referring to FIG. 2 of the drawings, it will be seen that the stirring block which may be either circular or square is provided with a plurality of transducers 21 and electrical conductors 22 which lead therefrom through the body of the stirring block 16 and connect with amplifiers 23 and meters 24. Metal members 25 are also embedded in the stirring block 16 in spaced relation to the transducers 21, which form the sensors in the form of the invention illustrated in FIG. 2, the metal members 25 being so disposed that erosion of the walls of the conical passageway 17 will cause the wearing away or melting away of portions of the metal members 25 directly proportional to the wearing away of the material of the stirring block 16, thus changing the magnetic fields of the metal members 25 as they become smaller. The transducers 21 are Hall Effect transducers which produce a signal directly proportional to the magnetic field of the metal members 25. After passage through the amplifying circuit comprising the conductors 22 and preamplifiers 23, the signal from the Hall Effect transducers 21 is sent to the meters 24 which accurately indicate the metal members 25 to transducers 21 dimension. The dictionary definition of the Hall effect is "Disturbance of the lines of current flow in a conductor due to the application of a magnetic field, leading to an electric potential gradient transverse to direction of current flow". The meters 24 accurately indicate this dimension and therefore the degree of erosion or wear of the conicial passageway 17 in the stirring block 16.

It will occur to those skilled in the art that analog circuitry may be provided in connection with the meters to cause an alarm signal to sound thereby warning of the critical wearing away of the material of the stirring block.

In FIG. 2 of the drawings, the conical plug 18 is shown provided with secondary transducers 26 spaced with respect to secondary metal members 27 also embedded in the plug 18, the transducers 26 being connected by electrical conductors 28 to a preamplifier 29 and one of the meters 24. Wearing away of the ceramic material of the plug 18 will wear, erode or melt portions of the metal members 27 in comparable degree to the wearing away or erosion of the plug 18 and the Hall Effect transducers 26 will produce a signal directly proportional to the distance between the remaining metal members 27 and the transducers which is then indicated by one of the meters 24.

It will be observed that the positioning of the sensors in the embodiment of the invention illustrated in FIG. 2 and hereinbefore described utilizes Hall Effect transducers and accompanying circuitry and metal members positioned in the stirring block 16 and plug 18 so that wearing away of portions thereof increase the distance of the remaining portions and thus change their magnetic fields with respect to the transducers.

One of the common failures in stirring block installations in molten metal ladles has been the separation of the stirring block body from the refractory lining of the ladle.

In FIG. 2 of the drawings, the stirring block is provided with a cutaway area around its upper outer periphery so as to form a shoulder 28 continuously thereabout and the refractory bricks forming the refractory lining 11 of the ladle are positioned partially on the shoulder 28 so as to forcibly position the stirring block 16 in desired location in the ladle. The arrangement is such that cracks that commonly occur between a stirring block and the refractory lining in a ladle are limited so that molten metal in the ladle cannot follow the same downwardly and emerge from the ladle in the area around the tube 15 through which the stirring gas is being introduced.

It will occur to those skilled in the art that the stirring block which may be either square or circular, provided with the shoulder 28 thereabout, will thus be forcibly held in desired position in the ladle by the weight of the refractory lining and by the pressure of the molten metal on the lining as well as on the stirring block itself and that the shoulder 28 forms a ledge which enables the stirring block to be keyed into the refractory brick work lining to effectively prevent metal penetration thereabout.

Figure 3:
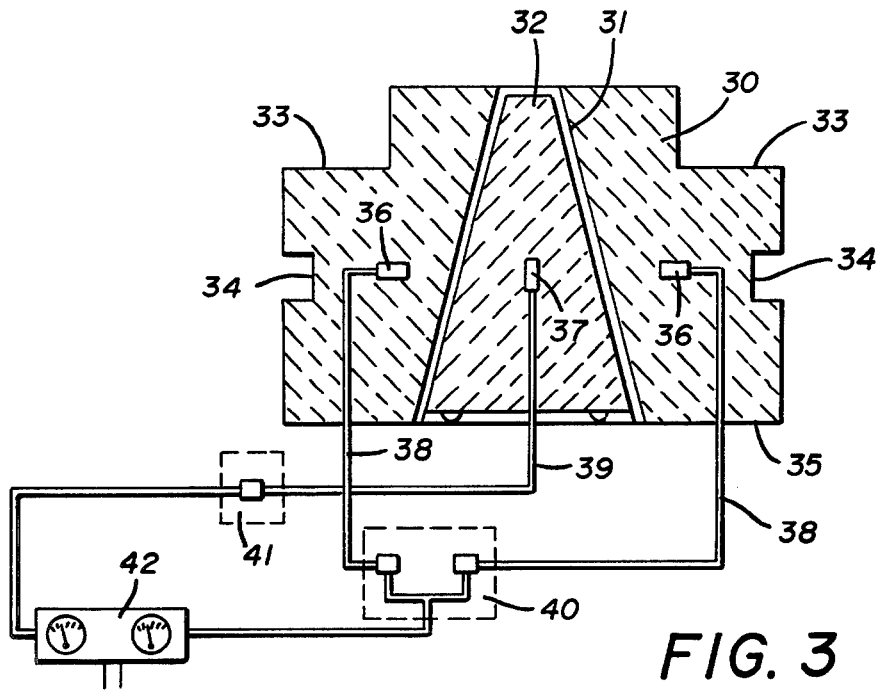
FIG. 3 is a cross sectional elevation of a stirring block having a modified shape with a plug disposed therein and heat sensors in the block and plug in a circuit indicating temperature variations thereof.

By referring now to FIG. 3 of the drawings, a modification of the invention may be seen, first in the formation of the stirring block itself, which is indicated in FIG. 3 by the numeral 30 provided with a conical central passageway 31 in which a plug 32 is positioned so as to form the usual gas passageway thereabout. The stirring block 30 may be round or square and it has an outer upper cutaway area defining a continuous shoulder or ledge 33 thereabout so that it may be incorporated in the brick work or rammed lining of a molten metal ladle and held securely in place by the lining. The stirring block 30 of FIG. 3 is also provided with a continuous groove 34 around its exterior spaced inwardly of the ledge 33 and above the bottom 35 of the stirring block. Heat sensors 36 are embedded in the stirring block and a secondary heat sensor 37 is embedded in the conical plug 32. Electrical conductors 38 and 39 lead from the heat sensors 36 and 37 to preamplifiers 40 and 41 and extend to meters 42. The heat sensors 36 may be any suitable thermocouple or like device capable of originating a signal upon change in temperature.

The circuitry, including the preamplifiers and the meters 42, thus provides a ready indication of the wearing away of the stirring block 30 and/or the conical plug 32 therein as wearing away or erosion of the surfaces of the conical passageway 31 or the exterior surfaces of the conical plug 32 reduces the volume and area of these respective elements with a corresponding increase in temperature which is detected by the sensors 36 and 37 and provides a read out on the meters 42 readily indicating the condition of the stirring block and/or the plug therein and in particular whether or not there is enough of the block still remaining to safely use the ladle again before replacing the block.

In addition to providing stirring blocks of novel configuration and sensors therein indicating the degree of wear thereof, the amount of wear or erosion is directly affected by the refractory materials used in forming the stirring block and the plug which may be either solid or porous as desired. For example, using high alumina or high zoricon or any combination of high melting point refractories, preferably rammed or cast in a direction opposite to that of the wear pattern of the molten metal, the density of the stirring blocks and plugs also affects the life as high density materials erode or wear at a slower rate than those materials of lesser density.

Figure 4:
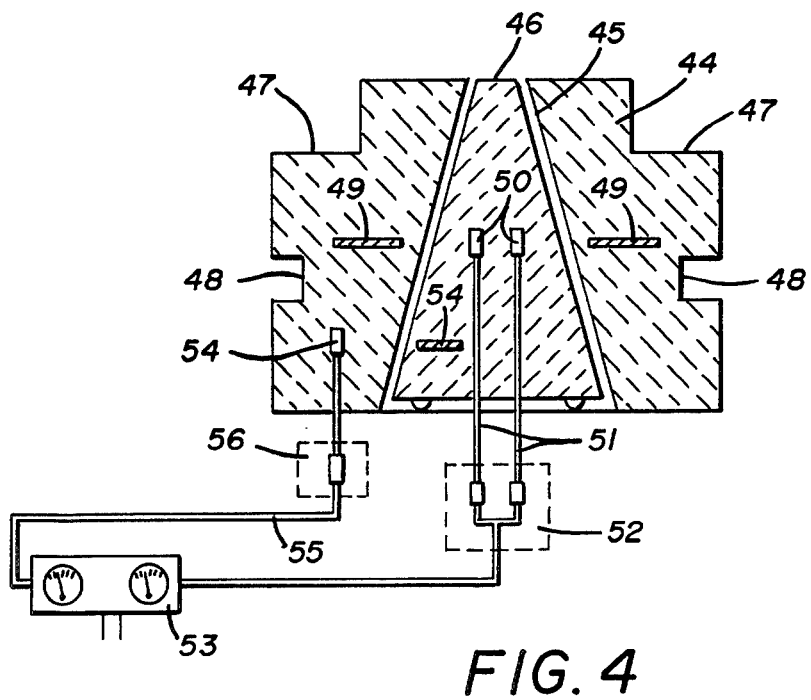
FIG. 4 is a cross sectional elevation of a stirring block of modified shape and a plug therein, the block and plug incorporating metal members embedded therein and Hall Effect transducers positioned so as to vary the output of the transducer devices upon the wearing or melting away of the metal members and a circuit for remotely indicating the variable output.

Be referring now to FIG. 4 of the drawings, a further modification of the invention may be seen in that a stirring block 44 having a conical passageway 45 therethrough and provided with a solid or a porous refractory plug 46 has a cutaway area about its upper outer surface forming a shoulder or ledge 47 and a peripheral groove 48 thereabout, both of which enable it to be keyed into the brick work or rammed lining of the molten metal ladle.

In FIG. 4 of the drawings, metal members 49 are embedded in the stirring block 44 in generally horizontal position with their inner opposed ends in close proximity to the central conical passageway 45. Sensors 50 are embedded in the conical plug 46 at substantially the same level as the metal members 49 in the block 44. Electrical conductors 51 extend through a preamplifier 52 to meters 53. A secondary metal member 54 is embedded in the conical plug 46 in substantially spaced relation to the sensors 50 which are Hall Effect transducers and a sensor 54, which is a Hall Effect transducer, is embedded in the block 44 on a common plane with the metal member 54. An electrical conductor 55 extends through a preamplifier 56 to the meters 53. In this form of the invention, wearing away of the stirring block 47 in the area of the upper surface or the passageway 45 therethrough or the wearing away of the plug 46 therein will be sensed by the transducers 50 and 54 and indicated by the meters 53 thus conveniently indicating the amount of the stirring block remaining and whether or not it is safe to continue to use the ladle or alternately necessary to replace the stirring block 44 and/or the conical plug 46 thereof.

Those skilled in the art will observe that while a limited number of transducers or other sensors, such as thermocouples, have been described in connection with the present invention, it is possible and sometimes desirable to incorporate a greater number of such sensors in the stirring blocks and/or conical plugs and that they may be located in various locations as desired and that the electrical conductors by which they communicate with the amplifying means and meters may be encased in metal tubes embedded in the devices all without departing from the spirit of the invention.

While the present invention has been described with a degree of particularity, it should be appreciated that modifications and alterations other than those disclosed may be made therein without departing from the spirit or scope of the invention as set forth in the appended claims.

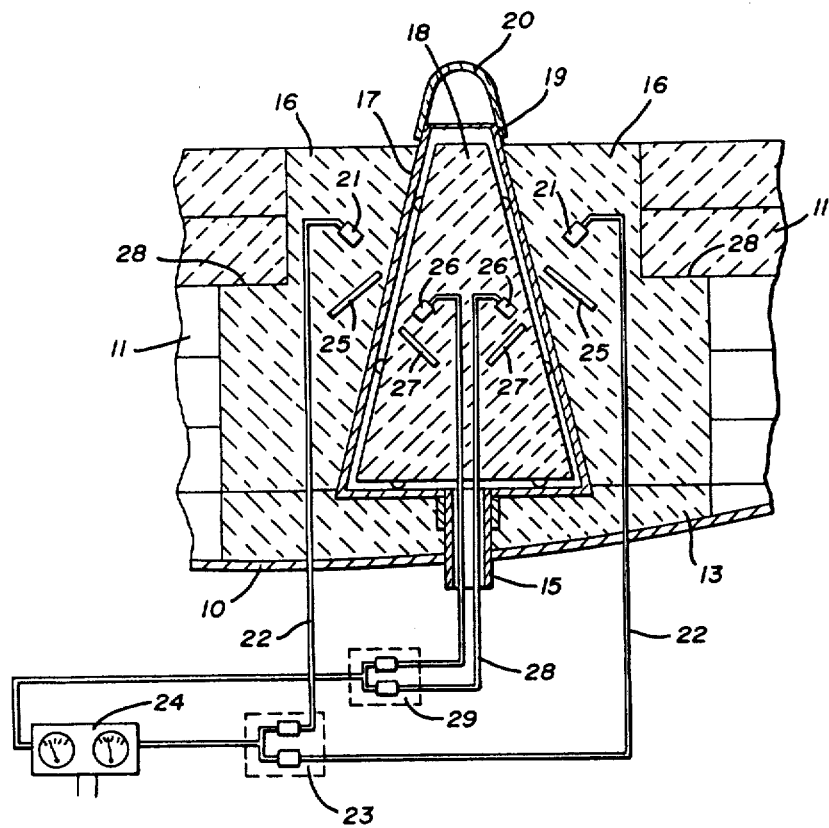

What I claim is:

1. A system for monitoring wear of a stirring block and a plug disposed in a passageway therein in a molten metal ladle, said system comprising a first metal member and a first Hall effect transducer for producing a first output representing the area in at least one location in said stirring block; a second metal member and a second Hall effect transducer for producing an output representing the area in at least one location in said plug; circuitry for monitoring said first and second Hall effect transducer outputs and producing signals when the area of either of said metal members changes a predetermined value.

2. The system for monitoring wear of a stirring block and a plug disposed in a passageway therein in a molten metal ladle set forth in claim 1 and wherein said first and second metal members are located in areas subject to erosion so as to be reduced in size by said erosion.

3. The system for monitoring wear of a stirring block and a plug disposed in a passageway therein in a molten metal ladle set forth in claim 1 and wherein the location of said first metal member is in an area of said stirring block subject to more rapid erosion and/or wear than the remainder of said stirring block.

4. The system for monitoring wear of a stirring block and a plug disposed in a passageway therein in a molten metal ladle set forth in claim 1 and wherein the location of said second metal member is in an area of said plug subject to more rapid erosion and/or wear than the remainder of said plug.

5. The system for monitoring wear of a stirring block and a plug disposed in a passageway therein in a molten metal ladle set forth in claim 1 and wherein a plurality of said second sensors are positioned in a plurality of spaced locations in said plug and wherein said circuitry for monitoring said second sensors interconnects said plurality thereof.

6. The system for monitoring wear of a stirring block and a plug disposed in a passageway therein in a molten metal ladle set forth in claim 1 wherein a refractory lining is positioned in said molten metal ladle and said stirring block is located in said refractory lining and wherein a portion of said refractory lining overlies a portion of said stirring block so as to insure the positioning of said stirring block in predetermined relation to molten metal in said molten metal ladle.

7. A system for monitoring wear of a stirring block and a plug disposed in a pasageway therein in a molten metal ladle wherein a plurality of first metal members are positioned in a plurality of spaced locations in said stirring block and wherein a plurality of Hall effect transducers are positioned in spaced relation to said first metal members and wherein a plurality of second metal members are positioned in a plurality of spaced locations in said plug and wherein a plurality of Hall effect transducers are positioned in spaced relation to said second metal members and wherein circuitry interconnects said plurality of Hall effect transducers, devices in said circuitry for producing signals when either said first metal members or said second metal members are partially eroded by molten metal in said ladle.

* * * * *

UNITED STATES PATENT AND TRADEMARK OFFICE
CERTIFICATE OF CORRECTION

PATENT NO. : 4,481,809

DATED : November 13, 1984

INVENTOR(S) : Micheal D. LaBate

It is certified that error appears in the above-identified patent and that said Letters Patent is hereby corrected as shown below:

The title page showing the illustrative figure should be deleted to appear as per attached title page.

Signed and Sealed this

Sixteenth Day of July 1985

[SEAL]

Attest:

DONALD J. QUIGG

Attesting Officer  Acting Commissioner of Patents and Trademarks

United States Patent [19]

LaBate

[11] Patent Number: 4,481,809
[45] Date of Patent: Nov. 13, 1984

[54] METHOD AND APPARATUS FOR MONITORING EROSION IN GAS STIRRING DEVICES IN MOLTEN METAL LADLES

[76] Inventor: Micheal D. LaBate, 115 Hazen Ave., Ellwood City, Pa. 16117

[21] Appl. No.: 527,362

[22] Filed: Aug. 29, 1983

[51] Int. Cl.³ ............................................. G01N 17/00
[52] U.S. Cl. .......................................... 73/86; 266/99
[58] Field of Search ................... 73/86; 374/7; 266/99

[56] References Cited

U.S. PATENT DOCUMENTS

| | | | |
|---|---|---|---|
| 2,915,305 | 12/1959 | Craig | 73/86 |
| 3,024,657 | 3/1962 | Brown | 266/99 |
| 3,856,284 | 12/1974 | Hoyer | 266/99 |
| 3,898,366 | 8/1975 | Aurini | 266/99 |
| 4,249,719 | 2/1981 | Knuppel et al. | 266/99 |

FOREIGN PATENT DOCUMENTS 82078  6/1983  European Pat. Off. .

Primary Examiner—S. Clement Swisher
Attorney, Agent, or Firm—Harpman & Harpman

[57] ABSTRACT

A method and apparatus are disclosed for monitoring the condition of the stirring block and solid plug therein as incorporated in the normal refractory brick lining of a molten metal ladle to provide a structure through which gas can be introduced into the molten metal, the method utilizes heat sensors and/or Hall Effect transducers embedded in the stirring block and/or solid plug therein in connection with apparatus providing a warning of critical wear and/or erosion in the gas stirring devices by the molten metal in the ladle. An appropriately shaped stirring block provides for the positioning of some of the normal refractory brick lining of the ladle partially thereover so as to eliminate loosening or cracking of the stirring block and the undesirable escaping of molten metal from the ladle.

7 Claims, 4 Drawing Figures